(12) United States Patent
Dirisio

(10) Patent No.: US 11,272,891 B2
(45) Date of Patent: *Mar. 15, 2022

(54) MAGNETIC BRAKING SYSTEM AND METHOD

(71) Applicant: CARESTREAM HEALTH, INC., Rochester, NY (US)

(72) Inventor: Anthony Dirisio, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 139 days.

This patent is subject to a terminal disclaimer.

(21) Appl. No.: 16/683,622

(22) Filed: Nov. 14, 2019

(65) Prior Publication Data

US 2020/0155091 A1 May 21, 2020

Related U.S. Application Data

(60) Provisional application No. 62/769,055, filed on Nov. 19, 2018.

(51) Int. Cl.
| | |
|---|---|
| *A61B 6/00* | (2006.01) |
| *A61B 6/10* | (2006.01) |
| *F16D 55/02* | (2006.01) |
| *F16D 65/18* | (2006.01) |
| *F16D 121/20* | (2012.01) |
| *G03B 42/02* | (2021.01) |
| *H05G 1/02* | (2006.01) |

(52) U.S. Cl.
CPC ............ *A61B 6/105* (2013.01); *A61B 6/4405* (2013.01); *A61B 6/4458* (2013.01); *F16D 55/02* (2013.01); *F16D 65/186* (2013.01); *F16D 2121/20* (2013.01); *G03B 42/02* (2013.01); *H05G 1/02* (2013.01)

(58) Field of Classification Search
CPC ......... A61B 6/00; A61B 6/4405; A61B 6/105; A61B 6/4458; A61B 6/4452; A61B 6/4476; H05G 1/02; F16D 55/02; F16D 65/186; F16D 2121/20; F16D 2121/22; F16D 63/008; F16D 59/02; G03B 42/02
See application file for complete search history.

(56) References Cited

U.S. PATENT DOCUMENTS

| | | | | |
|---|---|---|---|---|
| 4,964,152 | A * | 10/1990 | Kaul | ............. A61B 6/447 378/197 |
| 8,465,203 | B2 * | 6/2013 | Barker | ............. A61B 6/447 378/197 |
| 8,876,379 | B2 | 11/2014 | DiRisio et al. | |
| 2003/0217901 | A1 | 11/2003 | Carlson | |
| 2016/0069439 | A1 | 3/2016 | Davies | |
| 2020/0155083 | A1 * | 5/2020 | Dirisio | ............. A61B 6/4458 |
| 2020/0155090 | A1 | 5/2020 | DiRisio | |
| 2020/0155091 | A1 | 5/2020 | DiRisio | |

* cited by examiner

*Primary Examiner* — Jurie Yun

(57) ABSTRACT

A mobile radiography system includes a wheeled transport frame and a vertical column mounted on the transport frame. A boom is attached to the vertical column and to an x-ray tube head. A boom carriage allows movement of the boom along a track in the vertical column and includes a magnetic mechanism to lock the boom in the track at a desired height. An electromagnetic coil in the boom carriage is configured to disable the magnetic lock mechanism to allow vertical movement of the boom along the track.

15 Claims, 4 Drawing Sheets

MAGNETIC BRAKING SYSTEM AND METHOD

CROSS REFERENCE TO RELATED APPLICATIONS

This application claims priority to U.S. Patent Application Ser. No. 62/769,055, filed Nov. 19, 2018, in the name of Dirisio et al., and entitled BRAKING SYSTEM AND METHOD, which is hereby incorporated by reference herein in its entirety.

This application is related in certain respects to U.S. Pat. No. 8,876,379 B2, filed Apr. 11, 2011, in the name of Dirisio et al., and entitled COLLAPSIBLE COLUMN MOVEMENT APPARATUS FOR MOBILE X-RAY DEVICE, which is hereby incorporated by reference herein in its entirety.

BACKGROUND OF THE INVENTION

The invention relates generally to the field of medical imaging, and in particular to portable radiographic imaging apparatus. More specifically, the invention relates to a mobile radiography apparatus including improved operational features.

Mobile carts are employed in medical facilities to move medical equipment between locations. One type of mobile cart includes an x-ray source used to capture digital x-ray images in a digital radiographic detector. Mobile x-ray apparatus are of particular value in intensive care apparatus (ICU) and other environments where timely acquisition of a radiographic image is important. Because portable carts can be wheeled around the ICU or other area and brought directly to the patient's bedside, a portable x-ray imaging apparatus allows an attending physician or clinician to have recent information on the condition of a patient and helps to reduce the risks entailed in moving patients to stationary equipment in the radiological facility.

The discussion above is merely provided for general background information and is not intended to be used as an aid in determining the scope of the claimed subject matter.

BRIEF DESCRIPTION OF THE INVENTION

A mobile radiography system includes a wheeled transport frame and a vertical column mounted on the transport frame. A boom is attached to the vertical column and to an x-ray tube head. A boom carriage allows movement of the boom along a track in the vertical column and includes a mechanism to lock the boom in the track at a desired height. An electromagnetic coil in the boom carriage is configured to disable the lock mechanism to allow vertical movement of the boom along the track.

In one embodiment, a mobile radiography system includes a transport frame having wheels attached thereto for rollably transporting the system. A vertical column is mounted on the transport frame and includes a vertical track with a vertical brake plate. A boom is attached horizontally to the vertical column by a boom carriage that travels along the track. An x-ray tube head is attached to the boom and can be raised and lowered as the boom carriage rides along the vertical track. The boom carriage includes a brake pad, a permanent magnet to press the brake pad against the vertical brake plate to prevent vertical movement of the boom carriage along the track, and an electromagnetic coil to generate a magnetic field to counteract the permanent magnet and to allow vertical movement of the boom carriage along the track.

In another embodiment, a brake assembly includes an elongated brake plate, a brake mechanism configured to freely travel parallel to the brake plate when the brake mechanism is deactivated. The brake mechanism includes a pressure source and a brake pad to be pressed against the brake plate by the pressure source, and an electrically powered assembly configured to deactivate the brake mechanism when electric power is provided to the electrically powered assembly.

In another embodiment, a radiography system includes a vertical support column having a vertical track and a vertical brake plate therein. A boom carriage travels vertically along the vertical track, a horizontal boom is attached to the boom carriage, and an x-ray source is attached to the boom. The boom carriage includes a brake mechanism with a brake pad to be pressed against the vertical brake plate to prevent the boom carriage from traveling along the vertical track.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
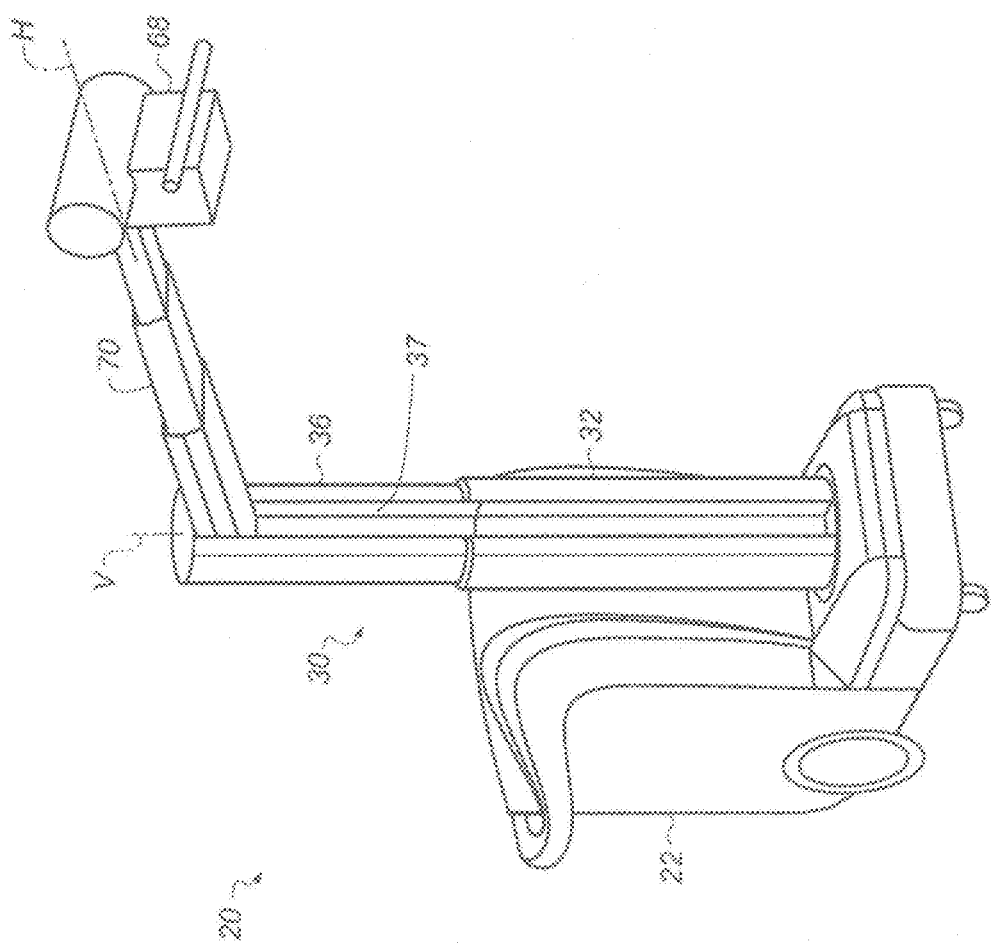
FIG. 1 is a perspective view of a mobile radiography apparatus.

With reference to FIG. 1 a mobile radiography apparatus 20 includes a telescoping boom 70 coupled to a telescoping, sectioned vertical column 30 according to one embodiment. An x-ray tube head 68 is in position for imaging, extended from vertical column 30, and supported, by boom 70 along a horizontal axis H that may be perpendicular, or slightly angled, relative to the vertical axis V. The mobile radiography apparatus 20 has a wheeled transport frame 22. Telescoping sectioned vertical column 30 is mounted on frame 22 parallel to the vertical axis V and has a vertically stationary base section 32 that seats against the frame 22. At least one movable section 36 of the vertical column 30 is vertically translatable within the stationary base section 32 to extend along the vertical axis V, so that boom 70 and x-ray tube head 68 can be set to a suitable height over a range of possible height settings. Boom 70 includes three tubular boom sections each having a relatively decreasing cross sectional area, respectively. One boom section, having the smallest cross sectional area, is rotatably attached to the x-ray tube head 68, to allow the tube head 68 to rotate about axis H. Boom 70 is attached to the vertical column 30 by a boom carriage, described herein below, to allow height adjustment of the boom 70 along a vertical track 37 in the vertical column 30.

Figures 2A, 2B:
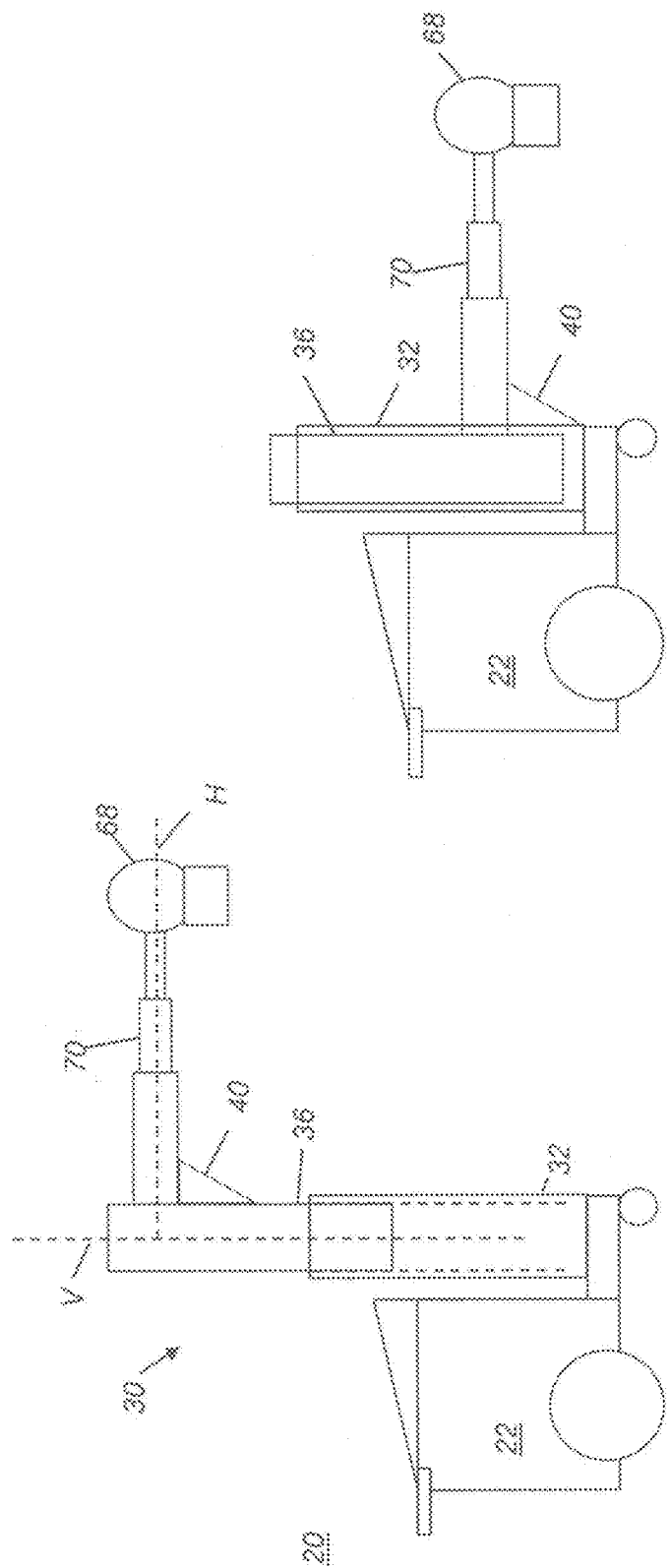
FIGS. 2A-2B are schematic side views of the mobile radiography apparatus of FIG. 1.

An operator can easily adjust a height of the boom 70 along vertical column 30 as well as a horizontal distance of the x-ray tube head 68 from the vertical column 30. As shown in FIG. 2A, stationary base section 32 of the vertical column 30 may include a hollow cavity or shaft allowing movable section 36 to travel vertically therethrough. The boom 70 may be raised to a height near the top of movable section 36 while movable section 36 is extended vertically within the shaft of stationary base section 32. A boom carriage 40 allows height adjustment of the boom 70 along a vertical track 37 in the vertical column 30, as described herein below. As shown in FIG. 2B, stationary base section 32 allows movable section 36 to travel vertically therethrough closer to the transport frame 22 where the stationary base section 32 is mounted to the transport frame 22. The boom 70 may be lowered to a height closer to the bottom of movable section 36 such as for imaging lower extremities of a subject.

Figure 3B:
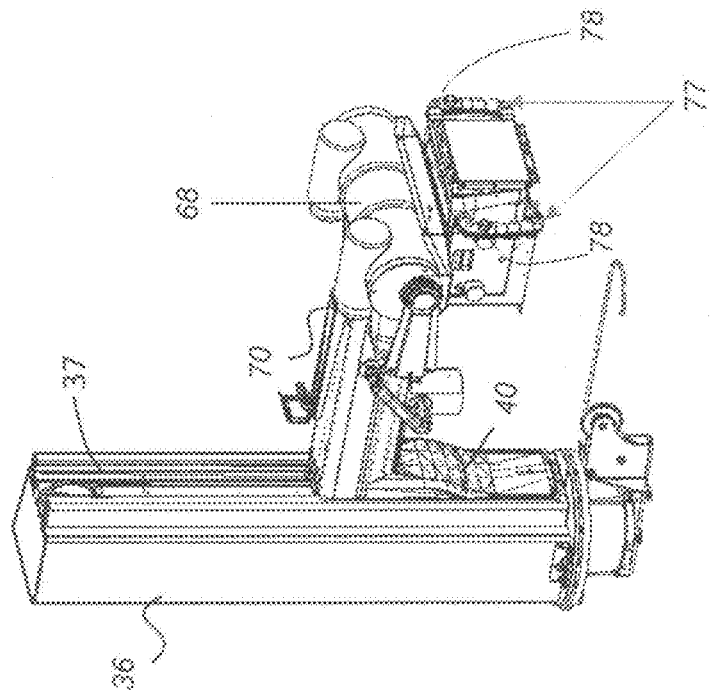
FIGS. 3A-3B are partial perspective views of the schematic views of FIGS. 2A-2B.
Figure 3A:
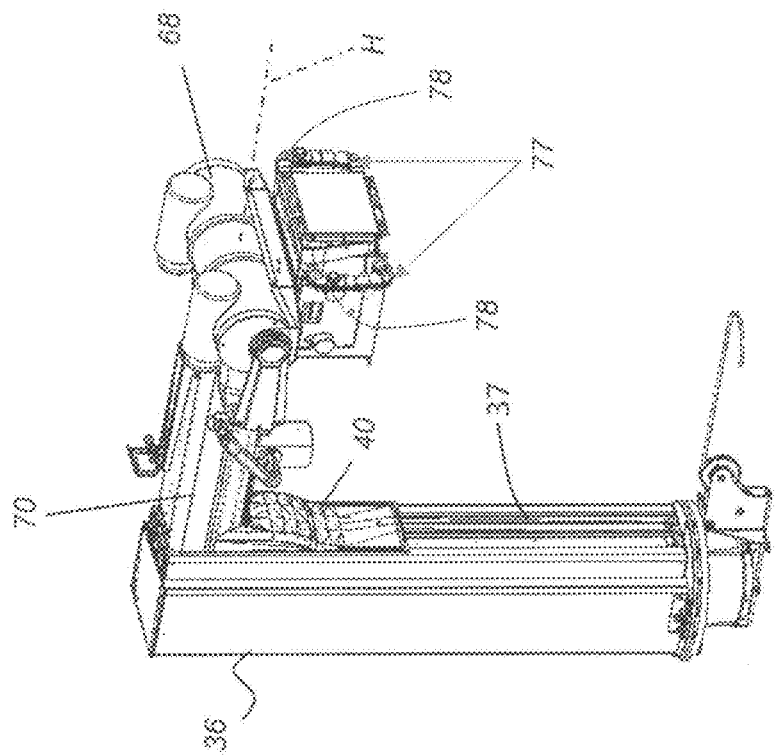

FIGS. 3A-3B, corresponding to FIGS. 2A-2B, respectively, show the movable upper section 36 in isolation together with boom 70 fully raised and lowered, respectively. The boom carriage 40 is secured to boom 70 and to a track 37 in the movable upper section 36. Handles 77 are attached to the tube head 68 to allow an operator to manually adjust a height of the tube head 68 by moving the boom 70 vertically along the track 37, to extend and retract the tube head 68 away and toward the vertical column 30 by operation of the boom 70 as described herein, and to rotate the tube head 68 about a horizontal axis H. Control switches 78 are positioned, one on each of the handles 77, for controlling vertical movement of the boom 70 vertically along the track 37, as described hereinbelow.

It is beneficial to allow the fullest possible range of vertical heights for the x-ray source in a portable system, from above shoulder height of the imaging technician to relatively low elevations, such as might be beneficial for imaging the foot or ankle of a patient. Applicants have noted that during the operation of raising and lowering the boom 70 there can be an improvement in the operation. For example, reducing noise, so as to not interfere or adversely affect the comfort of the patient and medical technician or improving smoothness of the operation so as to improve the usability and ease of comfort of the medical technician. Applicants have developed a brake assembly to improve the operation of the mobile radiography apparatus 20. One benefit is to eliminate/reduce noise which may occur when raising and/or lowering the boom 70. The boom 70 and the components employed to raise/lower the boom 70 have many contact points that slide against and contact each other during operation. Applicants' brake assembly, as described herein, mitigates undesirable noise issues.

Figure 4:
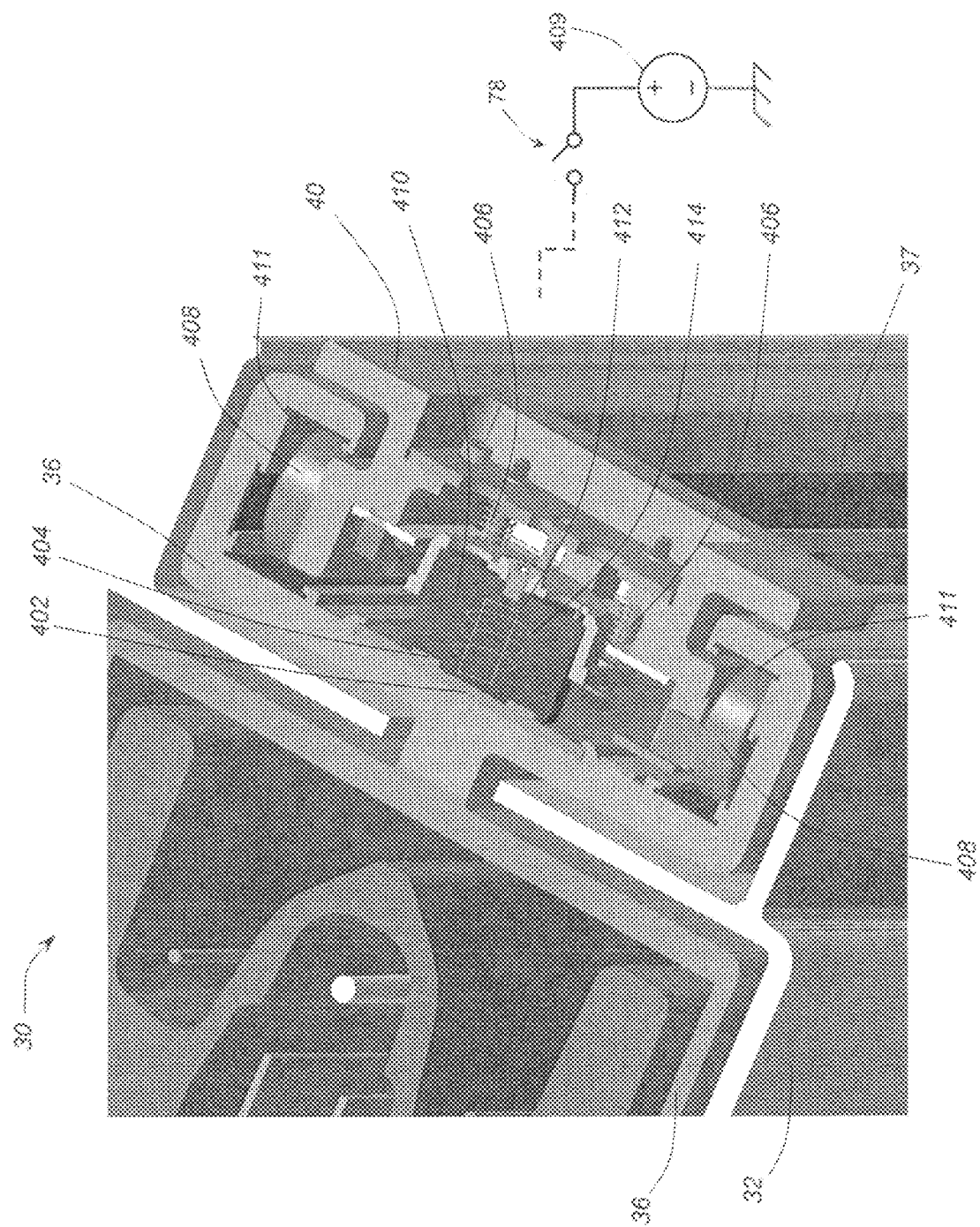
FIG. 4 is cross section view of the vertical column and boom carriage.

FIG. 4 illustrates a cross section of vertical column 30 and boom carriage 40, showing the boom carriage 40 secured within a vertical track 37 of the movable upper section 36 of the vertical column 30. The boom carriage 40 includes wheels 408 secured within wheel tracks 411 of the upper movable section 36 for facilitating vertical movement of the boom carriage 40. The boom carriage 40 further includes a magnetic brake assembly 410 attached therewithin and configured to be slightly movable toward and away from the brake plate 402. The magnetic brake assembly 410 includes a permanent magnet 412, an electromagnetic coil 414 and friction material, or brake pad, 404. The magnetic brake assembly 410 is formed in the shape of a cylinder having a circular recess in a side of the cylinder that faces brake plate 402, which brake plate 402 is made from a ferrous material. The friction material, or brake pad, 404 includes a circular shape for fitting within the circular recess of the magnetic brake assembly 410. The brake pad 404 is configured to extend beyond a face of the magnetic brake assembly 410 by about 0.001 (one-thousandth) to about 0.005 (five thousandths) of an inch. The permanent magnet 412 is configured to be attracted to brake plate 402 and thereby to press the brake pad 404 against the brake plate 402 by a magnetic force to provide a frictional resistance sufficient to prevent the boom carriage 40 from traveling vertically along the track 37. The frictional resistance provided by pressing the brake pad 404 against the brake plate 402 is configured to be sufficient to hold boom carriage 40 in place, and thereby boom 70, relative to movable upper section 36 to prevent unintended movement of boom 70 caused by, for example, gravitational force, vibrations or bumping.

The brake plate 402 comprises a vertical strip made of ferrous material extending along the vertical length of an inside surface of the movable upper section 36, and may be attached thereto by suitable means such as screws. The brake plate 402 may be considered as part of the movable upper section 36. In one embodiment, the magnet 412 may be made from neodymium, an alloy of neodymium, iron and boron (NdFeB). The electromagnetic coil 414 of the magnetic brake assembly 410 is configured to counteract the magnetic field of the permanent magnet 412 when the electromagnetic coil 414 is powered to generate a magnetic field opposing that of the permanent magnet 412, thereby releasing the brake pad 404 from pressing against the brake plate 402 and allowing manual vertical movement of the boom carriage 40 along the track 37. A power source 409 may be connected to the electromagnetic coil 414 using one or both of the switches 78 in the handles 77 to provide power to, and thereby activate, the electromagnetic coil 414 and release the brake pad 404 from pressing against the brake plate 402. One or both of the switches 78 may be configured to connect power source 409 to the electromagnetic coil 414 when one or both of the switches 78 are depressed and to disconnect power source 409 from the electromagnetic coil 414 when one or both of the switches 78 are released.

The boom carriage 40 further includes a pair of springs 406 which are attached to the boom carriage 40 and to the magnetic brake assembly 410 to maintain a constant contact of the brake pad 404 lightly against brake plate 402 when the electromagnetic coil 414 is activated. This prevents a noisy impact of the brake pad 404 against the brake plate 402 when the electromagnetic coil 414 is deactivated such as when an operator releases the buttons 78. Thus, in a typical procedure for raising or lowering the boom 70, an operator may grasp the handles 77; then manually depress either or both the control switches 78 to electrically connect the power source 409 to the electromagnetic coil 414, thereby activating the coil 414 and generating an electromagnetic field of sufficient strength to negate the magnetic field of the permanent magnet 412 to allow free vertical movement of the boom carriage 40 within the track 37 to raise and lower the boom 70 to a desired height; then release the control switches 78 to deactivate the electrically conductive coil 414 so that the magnetic field of the permanent magnet 412 presses the brake pad 404 against the brake plate 402 to provide a frictional resistance against further unintended vertical movement of the boom carriage 40, thus maintaining the desired height of the boom 70. The brake pad 404 may be made from typical materials used for brake pads, such as a ceramic friction material, or a metallic or semi-metallic ceramic mixture including any one or more of iron, copper, steel or graphite bonded together.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A mobile radiography system comprising:
   a transport frame having wheels attached thereto for rollably transporting the system;
   a vertical column mounted on the transport frame, the vertical column comprising a vertical track, the vertical track comprising a vertical brake plate;
   a boom attached horizontally to the vertical column by a boom carriage configured to travel along the track; and
   an x-ray tube head attached to the boom,
   wherein the boom carriage comprises:
   a brake pad;
   a permanent magnet to press the brake pad against the vertical brake plate to prevent vertical movement of the boom carriage along the track; and
   an electromagnetic coil to generate a magnetic field to counteract a magnetic field of the permanent magnet and to allow vertical movement of the boom carriage along the track when the electromagnetic coil is activated.

2. The system of claim 1, wherein the boom carriage comprises a spring to bias the brake pad against the vertical brake plate when the electromagnetic coil is activated.

3. The system of claim 2, wherein the brake pad is positioned between the permanent magnet and the vertical brake plate.

4. The system of claim 3, wherein the electromagnetic coil releases the brake pad from pressing against the vertical brake plate when the electromagnetic coil is activated.

5. The system of claim 4, further comprising a power source electrically connectable to the electromagnetic coil for providing power to activate the electromagnetic coil.

6. The system of claim 5, further comprising a manually operable switch for electrically connecting the power source to the electromagnetic coil.

7. A brake assembly comprising:
   an elongated brake plate;
   a brake mechanism configured to freely travel parallel to the brake plate when the brake mechanism is deactivated, the brake mechanism comprising:
   a pressure source;
   a brake pad configured to be pressed against the brake plate by the pressure source; and
   an electrically powered assembly comprising an electromagnetic coil to generate a magnetic field configured to deactivate the brake mechanism when electric power is provided to the electromagnetic coil.

8. The brake assembly of claim 7, wherein the brake plate is fixed in position relative to the brake mechanism and the brake mechanism is attached to a movable carriage.

9. The brake assembly of claim 8, wherein the pressure source comprises a permanent magnet.

10. The brake assembly of claim 9, wherein the permanent magnet is configured to generate a first magnetic field, the electromagnetic coil is configured to generate a second magnetic field, and wherein the second magnetic field negates the first magnetic field when power is provided to the electrically powered assembly.

11. The brake assembly of claim 10, further comprising a power source and a switch, wherein the switch is configured to electrically connect the power source to the electrically powered assembly to provide power thereto.

12. A radiography system comprising:
    a vertical support column having a vertical track and a vertical brake plate therein;
    a boom carriage configured to travel vertically along the vertical track;
    a horizontal boom attached to the boom carriage; and
    an x-ray source attached to the horizontal boom,
    wherein the boom carriage comprises:
    a brake mechanism comprising:
    a brake pad, the brake mechanism configured to press the brake pad against the vertical brake plate to prevent the boom carriage from traveling vertically along the vertical track;
    a permanent magnet to press the brake pad against the vertical brake plate; and
    an electromagnetic coil to deactivate the brake mechanism, wherein a magnetic field generated by the electromagnetic coil counteracts a magnetic field of the permanent magnet when the brake mechanism is deactivated, and wherein the boom carriage is free to travel vertically along the vertical track when the brake mechanism is deactivated.

13. The system of claim 12, further comprising a power source to power the electromagnetic coil to generate the counteracting magnetic field.

14. The system of claim 13, further comprising a manual switch for connecting the power source to the electromagnetic coil to deactivate the brake mechanism.

15. The system of claim 14, wherein the manual switch is configured to disconnect the power source from the electromagnetic coil when the manual switch is manually released.

* * * * *